US011452585B2

United States Patent
Clauss

(10) Patent No.: US 11,452,585 B2
(45) Date of Patent: Sep. 27, 2022

(54) DEVICE AND METHOD FOR MEASURING A MOVEMENT OF A MANDIBLE

(71) Applicant: IGNIDENT GmbH, Ludwigshafen am Rhein (DE)

(72) Inventor: Petra Ina Clauss, Rottach-Egern (DE)

(73) Assignee: IGNIDENT GmbH, Ludwigshafen am Rhein (DE)

(*) Notice: Subject to any disclaimer, the term of this patent is extended or adjusted under 35 U.S.C. 154(b) by 291 days.

(21) Appl. No.: 16/081,779

(22) PCT Filed: Mar. 1, 2017

(86) PCT No.: PCT/EP2017/054762
§ 371 (c)(1),
(2) Date: Aug. 31, 2018

(87) PCT Pub. No.: WO2017/149010
PCT Pub. Date: Sep. 8, 2017

(65) Prior Publication Data
US 2019/0076226 A1    Mar. 14, 2019

(30) Foreign Application Priority Data

Mar. 1, 2016 (DE) .......................... 102016103655.2
Jan. 13, 2017 (DE) .......................... 102017200515.7

(51) Int. Cl.
*A61C 19/045* (2006.01)
*A61C 9/00* (2006.01)
(Continued)

(52) U.S. Cl.
CPC .......... *A61C 19/045* (2013.01); *A61B 5/1126* (2013.01); *A61B 5/4542* (2013.01);
(Continued)

(58) Field of Classification Search
CPC ....... A61C 19/04; A61C 19/045; A61C 19/05; A61C 19/052; A61C 9/004; A61C 9/0046;
(Continued)

(56) References Cited

U.S. PATENT DOCUMENTS 4,286,947 A * 9/1981 Daiberl .................. A61C 19/04
433/72
5,604,817 A * 2/1997 Massen .................. A61C 9/006
382/120
(Continued)

FOREIGN PATENT DOCUMENTS

| CN | 1960675 | 5/2007 |
| CN | 102499780 | 6/2012 |

(Continued)

OTHER PUBLICATIONS

SG Office Action in Singapore Appln. No. 11201807471Y, dated Dec. 17, 2019, 7 pages.
(Continued)

*Primary Examiner* — Heidi M Eide
(74) *Attorney, Agent, or Firm* — Fish & Richardson P.C.

(57) ABSTRACT

The invention relates to a device (1) for measuring a relative position and/or movement of a mandible (UK) relative to a maxilla of a patient, comprising an emitting coil (8) for emitting an electromagnetic measuring field (5), at least one mandible sensor (US1), said mandible sensor (US1) being placed and/or can be placed on teeth in the mouth (U1-U8) or in the mouth on a mandible device (UK). The mandible sensor (US1) is designed as a sensor at least for determining a position in a measuring field (5) and/or relative to the emitting coil (8), also comprising an evaluation device (3) for determining the relative position and/or relative movement of the mandible (UK) relative to the maxilla (OK) based on positions determined by the sensor (US1). The
(Continued)

sensor coil (8) is placed and/or can be placed outside of the mouth on the side or above the maxilla (OK). The invention also relates to a method for determining a relative position and/or movement of the mandible (UK) relative to a maxilla (OK) of a patient with a device (1), a device (X) for simulating and transferring a measured relative movement from the method and a holding device for at least one maxilla sensor (OS1) and/or at least one mandible sensor (US1).

18 Claims, 10 Drawing Sheets

(51) Int. Cl.
| | | |
|---|---|---|
| *A61B 5/11* | (2006.01) | |
| *A61B 5/00* | (2006.01) | |
| *A61C 11/00* | (2006.01) | |
| *A61C 11/06* | (2006.01) | |

(52) U.S. Cl.
CPC ............ *A61B 5/682* (2013.01); *A61C 9/0053* (2013.01); *A61C 11/003* (2013.01); *A61C 11/06* (2013.01)

(58) Field of Classification Search
CPC ....... A61C 11/003; A61C 11/06; A61C 11/00; A61B 5/4542; A61B 5/1126; A61B 5/682; A61B 6/145; A61B 34/20; A61B 2034/2051

See application file for complete search history.

(56) References Cited

U.S. PATENT DOCUMENTS

| | | | |
|---|---|---|---|
| 7,402,996 B2 | 7/2008 | Arai et al. | |
| 7,641,472 B2* | 1/2010 | Sears | A61C 7/14 |
| | | | 433/8 |
| 9,017,071 B2* | 4/2015 | Hultgren | G16H 50/50 |
| | | | 433/24 |
| 2003/0204150 A1 | 10/2003 | Brunner | |
| 2007/0252586 A1 | 11/2007 | Arai et al. | |
| 2009/0286195 A1* | 11/2009 | Sears | A61C 7/14 |
| | | | 433/8 |
| 2011/0053110 A1 | 3/2011 | Bando et al. | |
| 2013/0095941 A1* | 4/2013 | Bentley | H01Q 1/526 |
| | | | 473/223 |
| 2015/0289806 A1* | 10/2015 | Hoke | A61C 19/045 |
| | | | 433/180 |
| 2015/0289960 A1* | 10/2015 | Shigemoto | A61B 5/11 |
| | | | 433/27 |
| 2016/0128624 A1* | 5/2016 | Matt | A61B 5/1128 |
| | | | 600/301 |
| 2017/0184149 A1* | 6/2017 | Sutton | F16C 11/0604 |
| 2018/0008378 A1* | 1/2018 | Raghavan | A61C 7/12 |

FOREIGN PATENT DOCUMENTS

| | | |
|---|---|---|
| DE | 10218435 | 11/2003 |
| DE | 112005000700 | 3/2007 |
| EP | 1303771 | 12/2005 |
| JP | 2989600 | 12/1999 |
| JP | 2010-187708 | 9/2010 |
| WO | WO 1997036192 | 10/1997 |
| WO | WO 2005094677 | 10/2005 |
| WO | WO 2014050543 | 4/2014 |
| WO | WO 2014198873 | 12/2014 |
| WO | WO2017/149010 | 9/2017 |

OTHER PUBLICATIONS

International Search Report & Written Opinion in corresponding Application No. PCT/EP2017/054762, dated Aug. 8, 2017, pp. 1-19.

International Preliminary Report on Patentability in corresponding Application No. PCT/EP2017/054762, dated Sep. 13, 2018, pp. 1-22.

EPO Communication Pursuant to Article 94(3) in European Appln. No. 17707895.3, dated Mar. 19, 2020, 13 pages (with English Translation).

CN Office Action in Chinese Appln. No. 201780027203.1, dated Sep. 11, 2020, 23 pages (with English translation).

JP Office Action in Japanese Appln. No. 2018545144, dated Mar. 16, 2021, 17 page with English Translation.

JP Decision of Rejection in Japanese Appln. No. 2018-545144, dated Jan. 18, 2022, 8 pages with English Translation.

* cited by examiner

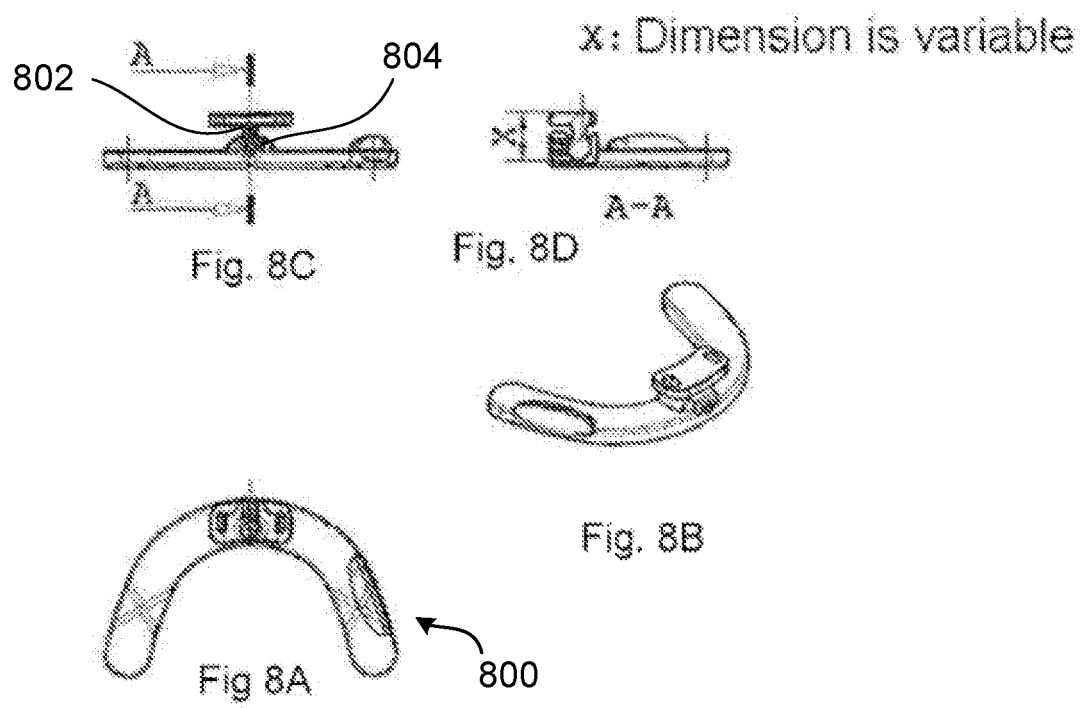
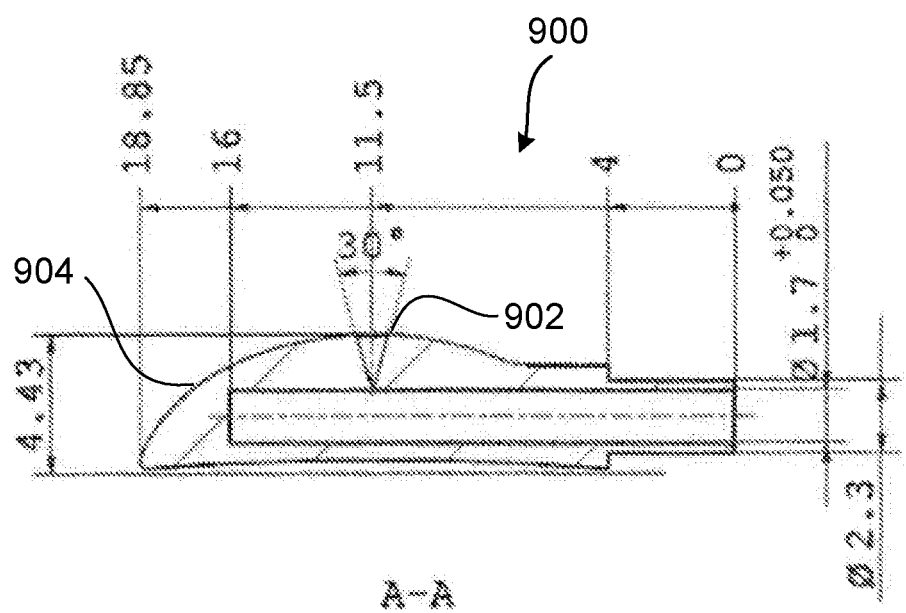

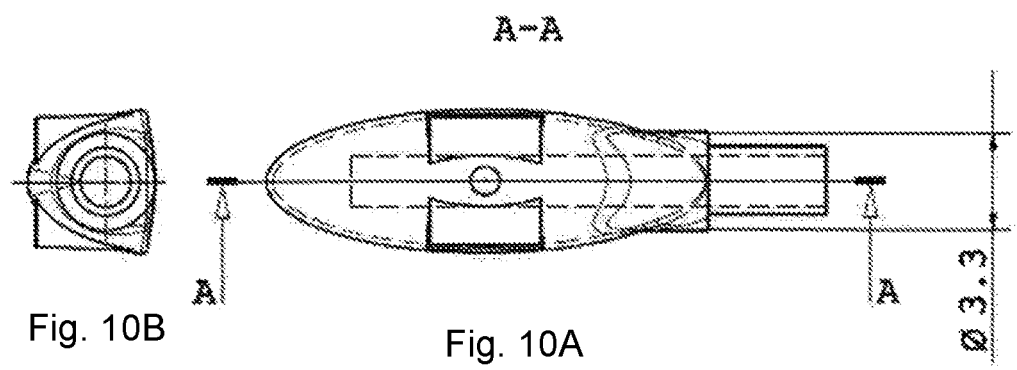
Fig. 10B
Fig. 10A
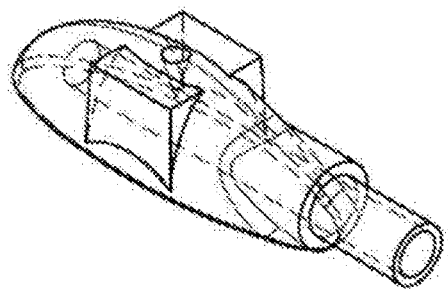
Fig. 11A
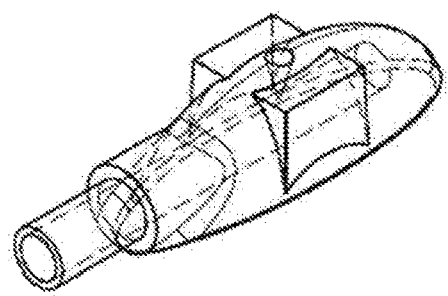
Fig. 11B

DEVICE AND METHOD FOR MEASURING A MOVEMENT OF A MANDIBLE

The invention relates to a device for measuring a relative position and/or relative movement of a mandible relative to a maxilla of a patient. The device comprises a transmitter coil for emitting an electromagnetic measurement field and at least one sensor, which is at least connected to the mandible. Furthermore, the device comprises an analysis unit, which determines the relative position and/or relative movement of the mandible relative to the maxilla on the basis of the sensor signals. The invention also relates to a corresponding method using this device, and also a device for simulating and transferring a measured relative movement from the method and a holding unit for at least one maxilla sensor and/or at least one mandible sensor.

Digital or physical impressions of the mandible and of the maxilla of a patient are required in dental technology for greatly varying purposes. One typical type of physical impression is, for example, the use of an impression apparatus, in particular an impression tray, wherein an impression of the maxilla teeth including soft tissue or the mandible teeth including soft tissue, respectively, is pressed into an impression material. It is also possible to acquire digital imprints of the teeth of the maxilla and the mandible by means of intraoral scanners and digital image processing.

Both types of generating the impressions of maxilla or mandible, respectively, have the restriction, however, that neither an articulation, in particular the intercuspation, nor the movement of the mandible in relation to the maxilla can be depicted. However, it is necessary, for example, when manufacturing dental prostheses to also take into consideration this movement of the mandible in relation to the maxilla. For this reason, the relationships between mandible, maxilla, and the mandibular joint are measured via aids, for example face bows, etc., and transferred to digital (virtual) or real articulators. However, these methods are comparatively inaccurate because of the indirect measurement of the movement. The movement can thus only be simulated according to estimates here.

A method and a device for three-dimensional movement analysis of tooth surfaces of the maxilla in relation to the mandible are presented in document DE 102 18 435 A1. The device has a maxilla sensor, which is arranged on a face bow and records the movement of a bite plate, which is fixedly connected to the maxilla. Furthermore, the device has a mandible sensor, which is fixedly connected mechanically to the mandible via an accessory. A position and thus also a movement of the mandible relative to the maxilla can be recorded by analysis of the signals of the maxilla sensor and the mandible sensor via a referencing of the sensors relative to the maxilla and to the mandible.

Document DE 11 2005 000 700 T5 discloses a device for measuring a position of a mandible relative to a maxilla, wherein magnetic field sensors and magnetic field generators are arranged in the mouth of the patient to determine the positions.

The invention is based on the object of proposing a device and a method for measuring a relative position and/or relative movement of a mandible relative to a maxilla of a patient, which are distinguished by a high measurement accuracy.

This object is achieved by a device as described herein, a method as described herein, a device for simulating and transferring a measured relative movement as described herein, and a holding unit for at least one maxilla sensor (OS1) and/or at least one mandible sensor (US1) as described herein. Preferred or advantageous embodiments of the invention result from the dependent claims, the following description, and the appended figures.

The subject matter of the invention is a device which is suitable and/or designed for measuring a relative position and/or relative movement of a mandible relative to a maxilla of a patient. The mandible preferably comprises no teeth, at least one tooth, several teeth, or all teeth. Alternatively or additionally, the maxilla comprises no teeth, at least one tooth, preferably several teeth, in particular all teeth. The device is used for the purpose of determining the relative position of the mandible relative to the maxilla of the patient. If multiple such relative positions are recorded in a chronological sequence, the device can thus also be used for the purpose of determining a relative movement of the mandible relative to the maxilla of the patient.

The device is based on an electromagnetic measuring principle. The device thus comprises at least one or precisely one transmitter coil, which is designed for emitting, in particular for generating, an electromagnetic measurement field. The transmitter coil is preferably placed in such a manner that the electromagnetic measurement field is overlaid and/or can be overlaid with a head of the patient, in particular the region of the mandible and the maxilla.

The device comprises at least one or precisely one mandible sensor, which is arranged intraorally, i.e., in the oral cavity, in particular completely in the oral cavity. The mandible jaw sensor is possibly arranged alternately on the teeth or on a mandible accessory of the mandible in each case. The latter is implemented in particular if no teeth are present at the desired positions.

Furthermore, the device preferably comprises at least one or precisely one maxilla sensor, wherein the maxilla sensor is also arranged intraorally, i.e., in the oral cavity, in particular completely in the oral cavity of the patient. In the same manner as the mandible sensor, the maxilla sensor can be arranged on the teeth or on a maxilla accessory of the maxilla, in particular for the case in which no teeth are present at the desired position.

The mandible is the important jaw metrologically, because it moves. The mandible sensor therefore records the relative movement. The maxilla sensor preferably forms a reference sensor to the mandible sensor. The maxilla sensor can additionally eliminate a head movement by computation via a computer program. This is also conceivable without a sensor, and therefore the mandible sensor can also record a relative movement without reference sensor in the maxilla.

The mandible sensor and the maxilla sensor—also referred to in summary hereafter as sensors—are designed as position sensors for respectively determining a position, in particular an absolute position, in the measurement field and/or relative to the transmitter coil. In particular, the sensors are designed to determine at least three translational degrees of freedom.

Such position sensors, which can determine a position in an electromagnetic measurement field, in particular an alternating measurement field, are known, for example, from document WO 97/36192 A1 or from document EP 1 303 771 B1, the disclosure content of which is incorporated in the present application via referencing.

Furthermore, the device comprises an analysis unit, which is particularly preferably designed as a digital data processing unit, for example a computer, microcontroller, etc., which is designed for determining the relative position and/or relative movement of the mandible relative to the maxilla on the basis of the positions determined by the sensors. After the sensors have been fixedly connected to the mandible or maxilla, respectively, and the positions can be acquired via the analysis unit, the position, in particular the relative position and/or relative movement between maxilla and mandible, is easily determinable from the provided data. The position of the sensors is preferably determined via an additional sensor unit (probe), and therefore they are referenceable in the analysis unit.

It is an advantage in this case that the sensors are arranged intraorally and thus no extensions or other apparatuses are required, which could corrupt the measurement result. Rather, the positions are recorded directly where they are most accurate, namely at the teeth of the mandible or the maxilla, respectively, or—if these teeth are not present—via accessories, which are also arranged close by. The metrology about the sensors, which are designed in particular as magnetic field sensors, has become established in the meantime, and therefore large measurement inaccuracies are also not to be expected here.

The device therefore represents a measuring system, via which the relative position and/or relative movement of mandible to maxilla can be recorded very accurately with a high accuracy and a low constructive expenditure.

A maxilla sensor (OS1) is preferably arranged and/or arrangeable intraorally on the teeth (O1-O8) or intraorally on a maxilla accessory of the maxilla (OK), In the case of a toothless jaw, the maxilla accessory of the maxilla (OK) and the mandible accessory of the mandible (UK) are preferably respectively designed as a bite plate for setting a vertical position (condyle position).

In this case, a bite plate is arrangeable on the maxilla and/or a bite plate is arrangeable on the mandible, wherein the respective bite plate is preferably U-shaped.

The respective bite plate preferably has one centrally arranged pin or multiple pins, wherein at least the pin has a ball having a threaded borehole, in which the pin is arranged such that it is at least vertically adjustable.

The ball is held on the respective bite plate by jaws and is movable in an articulated manner.

The ball is fixedly connected in this case to a foot, which is incorporated into the plate material. The vertical height is set by the dental technician according to mean values from the literature, for example for the maxilla OK 18 to 20 mm, for the mandible UK 16 to 18 mm.

The ball advantageously enables the bite plate to be set in the maxilla on the ala-tragus line and on the bipupillary line. Subsequently, the Ok bite plate is locked using a hex key. The ball in the mandible remains freely movable in this case until the patient has found a position. The UK bite plate screw is tightened thereafter.

Finally, the two plates are fixed with one another occlusally using silicone.

In the scope of the invention, it is proposed that the transmitter coil is arranged extraorally, in particular adjacent to the head or above the head of the patient. The measurement field therefore penetrates the head of the patient. The transmitter coil is particularly preferably arranged in a stationary manner and/or independently of the patient. This stationary arrangement of the transmitter coil independently of the patient has the advantage that the transmitter coil cannot move during the measurement and thus forms a very accurate reference.

The invention is based on the consideration that the magnetic field is applied more homogeneously if it is generated by a transmitter coil which does not have to be integrated into the oral cavity of the patient, but rather can be arranged outside the oral cavity nearly without any installation space restriction. It is also possible without the installation space restriction to select the power for the measurement field freely or nearly freely. Both advantages ultimately result in a more stable measurement field and thus more accurate measurement results. The transmitter coil can generate the measurement field via alternating current or via a pulsating direct current.

In one preferred embodiment of the invention, the transmitter coil is arranged laterally diagonally with respect to or above the patient or the measurement space in which the patient is to be positioned. In particular, the measurement field radiates through a cheek of the patient originating from the transmitter coil. This positioning has the advantage that only tissue parts of the patient have to be penetrated by the measurement field.

In one preferred embodiment of the invention, the sensors are moreover designed to determine at least two rotational degrees of freedom, preferably all three rotational degrees of freedom, or six degrees of freedom (three translational degrees of freedom and three rotational degrees of freedom) in the measurement field. The sensors are designed in particular as five DOF sensors (degrees of freedom) or even as six DOF sensors. In the design as five DOF sensors, all three translational degrees of freedom and two rotational degrees of freedom can be acquired. In the design as six DOF sensors, all three translational degrees of freedom and all three rotational degrees of freedom can be acquired. An improved measurement in turn takes place due to the acquisition of the rotational degrees of freedom, and therefore the measurement accuracy of the device can be further increased. In one exemplary embodiment, the sensors consist of two 5 DOF sensors, which thus become a 6 DOF sensor. Therefore, two measurement points in the mandible and two measurement points in the maxilla, i.e., four measurement points in the x, y, and z directions, can be recorded, to determine a relative movement therefrom.

In one particularly preferred configuration of the invention, alternately precisely two five DOF sensors or precisely one six DOF sensor are respectively arranged on the maxilla and on the mandible. In particular, precisely one six DOF sensor is arranged on the maxilla and precisely one six DOF sensor is arranged on the mandible.

In one preferred embodiment of the invention, one sensor, in particular one six DOF sensor, is respectively arranged in each case on the mandible and on the maxilla, in the premolar region, in particular diametrically opposing. If the mandible sensor is arranged on the right, the maxilla sensor is then positioned on the left or if the mandible sensor is arranged on the left, the maxilla sensor is then positioned on the right. The measurement accuracy is further improved by this arrangement, in particular in conjunction with the laterally arranged transmitter coil.

In one preferred embodiment of the invention, the smallest distance between the respective sensor and the tooth on which the sensor is arranged is preferably less than 0.5 cm and in particular less than 0.3 cm. Due to the close positioning of the sensors on the teeth, measurement errors because of distances or extensions between the sensors and the teeth are avoided.

In one preferred embodiment of the invention, the device has one holding unit per jaw, wherein the holding units are fastened on the mandible and/or on the maxilla and accommodate the respective sensors. The holding units thus form a mechanical connection between the teeth and the sensors. Alternatively thereto, the sensors can also only be fastened by material bonding on the jaw and/or on the teeth of the jaw. The respective holding units on the maxilla (OK) and/or the mandible (UK) are particularly preferably formed as a sensor shoe, which can be adhesively bonded onto the respective teeth.

The holding unit according to the invention for at least one maxilla sensor (OS1) and/or at least one mandible sensor (US1), in particular for use in the mentioned device for measuring a relative position and/or relative movement of the mandible (UK) relative to a maxilla (OK) of a patient, is fastenable on the maxilla (OK) and/or on the mandible (UK).

The holding unit is preferably designed as a sensor shoe, which can be adhesively bonded onto the respective teeth or onto a mandible accessory or bite plate of the mandible (UK) or a maxilla accessory or bite plate of the maxilla (OK).

The sensor shoe has at least one curved surface region and/or at least one position marking.

The position marking is preferably formed as an indentation or recess in the curved surface region of the sensor shoe facing away from the respective tooth.

More preferably, the position marking is formed as a conical recess, the tip of which defines a zero point of the relationship of the sensor to the relative position and/or relative movement of the mandible (UK) relative to the maxilla (OK).

In this case, the tip of the position marking is in a direct relationship to a planar surface region around the recess of the sensor shoe, wherein the sensor position is defined in relation to the relative position and/or relative movement of the mandible (UK) relative to the maxilla (OK).

The position marking is preferably arranged centrally on the sensor shoe.

The sensor shoe has at least one curved surface region facing toward the respective tooth or teeth and is designed for the interlocking accommodation of a maxilla sensor (OS1) and/or a mandible sensor (US1).

In one particularly preferred embodiment of the invention, the device comprises a digitizing unit for creating a digital, three-dimensional model of the maxilla and/or the mandible, wherein the holding units and/or the sensors are modeled in the model. For example, the digitizing unit can be designed as an intraoral scanner. In other embodiments of the invention, the maxilla and the mandible of the patient can also be mechanically or physically impressed and subsequently digitized in a 3D scanner. In both embodiments, however, it is provided that the holding unit and/or the sensors are also impressed and/or digitized, and therefore the relative position between the sensors and/or holding units and the maxilla and the mandible are unambiguously determined. Alternatively thereto, a further sensor unit (probe) is used. The position of the sensors in the mouth can therefore be determined and transferred into the digitizing unit. The sensor unit is in particular a sensor tip, using which an orientation point is recorded at each of at least 3 retrievable points. These points then reference to the sensors. Corresponding software computes the position of the adhesively bonded sensors.

In this manner, it is then possible during the subsequent data processing to determine not only the relative position and relative movement of the sensors in relation to one another as a movement of the mandible relative to the maxilla, but rather to model the contour of the teeth of the maxilla and the contour of the teeth of the mandible relative to one another.

A further subject matter of the invention relates to a method for determining the relative position and/or the relative movement of a mandible relative to a maxilla of the patient, wherein a device is used as was described above and/or as claimed in any one of the preceding claims. It is provided in the method that the sensors are arranged on the mandible and on the maxilla and sensor signals of the sensors are recorded. In a following step, a determination of the relative position and/or relative movement between the maxilla and the mandible is carried out on the basis of the sensor signals.

The method optionally comprises a step of creating a digital, three-dimensional model of the maxilla and/or the mandible, wherein the holding unit and/or the sensors are modeled in the model. In a further step, the data of the sensors are fused with the model of the maxilla and the mandible, in particular in the analysis unit, and therefore a model of the maxilla and the mandible is formed in various relative positions and/or in relative movement in relation to one another. In particular, the model comprises a movement sequence, wherein the movement sequence comprises multiple complex individual movement sequences such as opening, closing, chewing, etc. In this manner, movement paths of the mandible relative to the maxilla can be determined.

A device according to the invention for simulating and transferring a measured relative movement of a mandible (UK) relative to a maxilla (OK) of a patient from the mentioned method comprises a receiver for receiving a digital, three-dimensional model of the maxilla (OK) and/or the mandible (UK), wherein the holding units or sensor shoes and/or sensors for receiving data are positioned in the model, Further features, advantages and effects of the invention result from the following description of a preferred exemplary embodiment of the invention and the appended figures, in which:

FIG. 1a, b show a schematic top view of a maxilla or a mandible, respectively;

FIGS. 4-8D show various diagonal views of a Li-shaped bite plate for a maxilla or mandible;

FIGS. 9-11B show a schematic side view, top view, and diagonal view of a sensor shoe according to the invention;

Figure 1A:
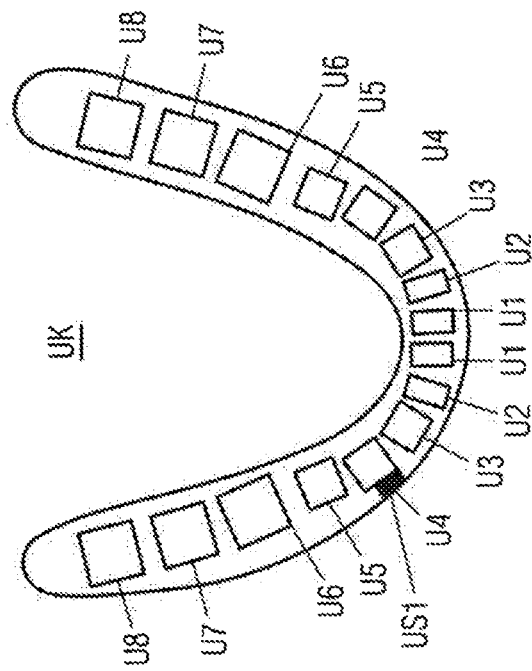
Figure 1B:
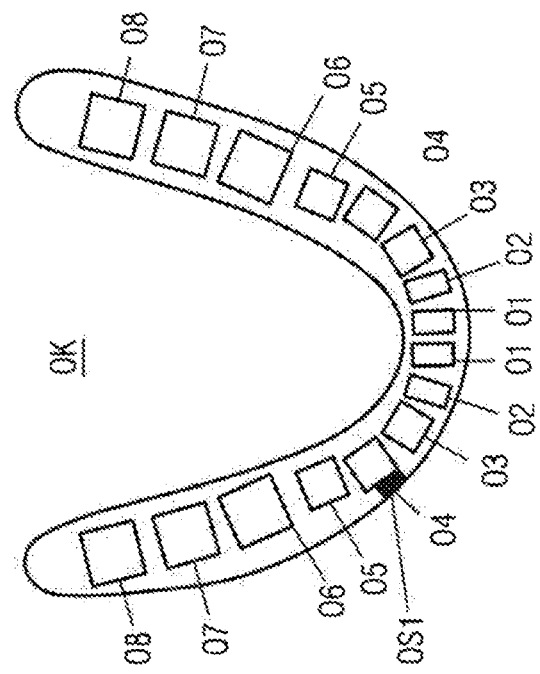

FIGS. 1a and 1b show, in a very schematic illustration, a maxilla OK (FIG. 1a) or a mandible UK (FIG. 1b), respectively, in a top view. In each of the jaws, sixteen teeth are shown, wherein the teeth of the maxilla OK are numbered continuously starting from the incisors with O1 and O2 via the premolars O4 and O5, via the molars up to the wisdom teeth with O8. In the same manner, the teeth of the mandible UK are numbered continuously from the incisors with U1 via the molars up to the wisdom teeth U8.

A sensor OS1 is arranged on the maxilla OK. Optionally, still further sensors can be provided. The maxilla sensor OS1 is fastened on one or both premolars O4 and/or O5. In a similar manner, a mandible sensor US1 is arranged on the mandible UK. The mandible sensor US1 is arranged on the premolars U4 and/or U5. Optionally, further sensors can be provided on the maxilla and/or on the mandible.

As may be inferred from the top view, the sensors OS1 or US1 are arranged directly at the respective teeth O4 or U4, respectively. The distance between the sensors and the teeth is less than 0.5 cm in each case. In particular, the sensors are positioned directly adjacent to the teeth. All sensors OS1 and US1 are arranged intraorally, i.e., in the oral cavity of the patient. The sensors are fixedly connected to the respective teeth, and therefore they each form a location reference to the teeth and thus to the maxilla OK or mandible UK, respectively.

The sensors are arranged on opposing halves of the jaws UK, OK and therefore one of the sensors is arranged on the left side of the jaw UK, OK and the other sensor is arranged on the right side of the jaw OK, UK.

Figure 2:
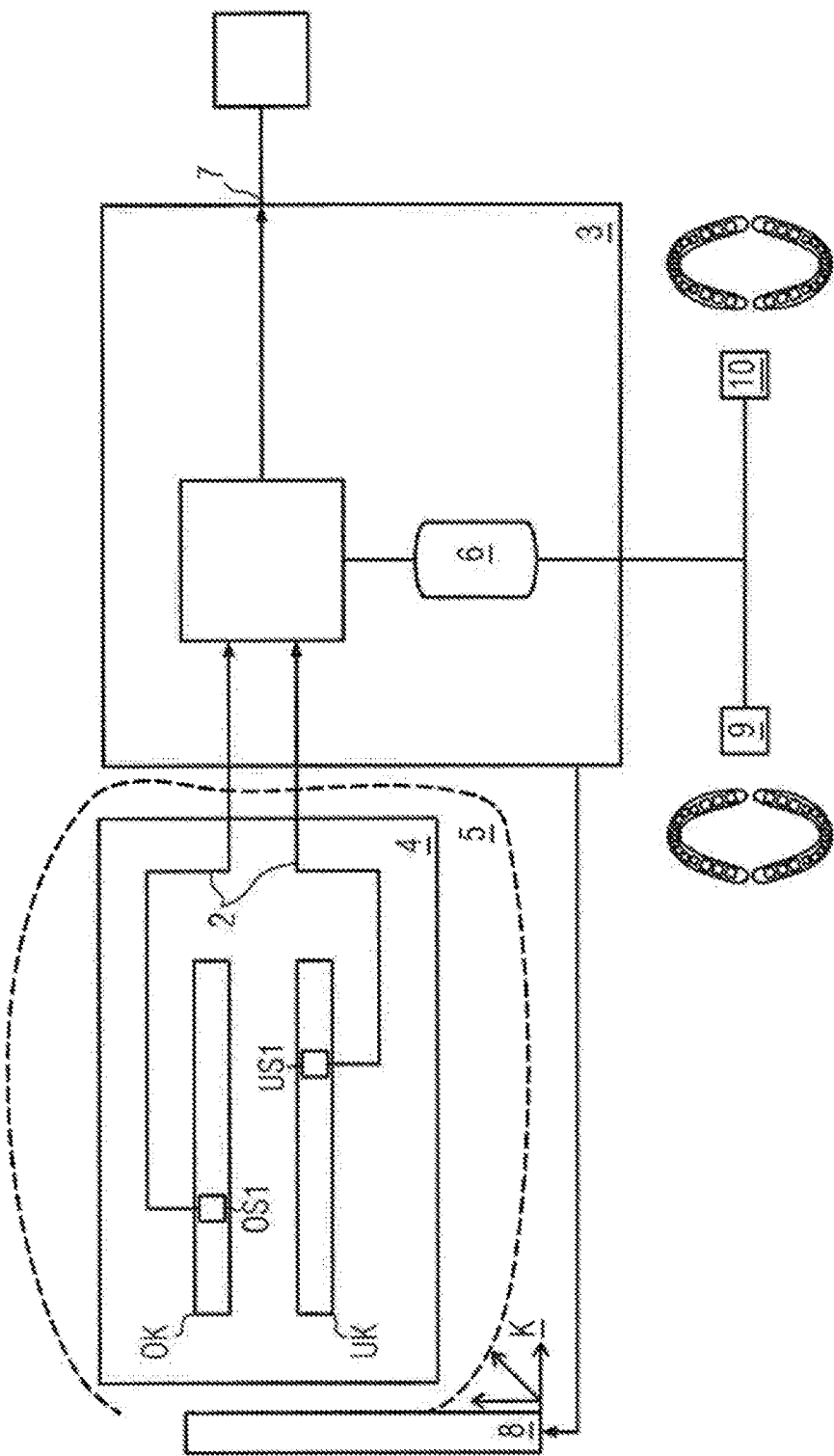
FIG. 2 shows a block diagram as an exemplary embodiment of a device according to the invention for measuring a relative position and/or relative movement of a mandible relative to a maxilla of a patient.

FIG. 2 shows a schematic block diagram of a device 1 for measuring the relative position and/or relative movement of the mandible UK relative to the maxilla OK. The relative position and/or relative movement is measured on a human, and therefore his or her natural jaw movement, for example during chewing, opening and closing, lateral movement to the left, lateral movement to the right, protrusion, and retrusion is recorded. The maxilla OK and the mandible UK with the sensors OS1 and US1 are shown very schematically once again on the left side. A very schematic frontal view is shown in this illustration, however. The sensors are connected via a cable connection 2 to an analysis unit 3, wherein sensor signals are fed from the sensors into the analysis unit 3 via the cable unit 2.

The device 1 has a transmitter coil 8, which is arranged adjacent to a head 4 of the patient (shown very schematically as a rectangle). The transmitter coil 8 generates an electromagnetic measurement field 5, which penetrates the head 4 of the patient and can be acquired by the sensors OS1 and US1.

The sensors are designed as magnetic field sensors and enable at least one absolute position in the measurement field 5 to be acquired. An absolute position of the sensors relative to the transmitter coil 8 can therefore be determined from the sensor signals. The absolute position can be output, for example, in a coordinate system K, which is connected fixed in place to the transmitter coil 3, as XYZ coordinates. Optionally, in addition to the absolute position, i.e., three translational degrees of freedom, the sensors can acquire further, in particular rotational, degrees of freedom. The sensors US1 and OS1 are each designed in this exemplary embodiment as a six DOF sensor and are thus magnetic field sensors which can record three translational and three rotational degrees of freedom in the magnetic field as the measurement field. The sensor signals are relayed via the cable unit 2 to the analysis unit 3 and further processed therein. The analysis unit 3 is designed, for example, as a computer or as another digital data processing unit.

The analysis unit 3 has a storage unit 6, in which a 3D model of the maxilla OK and the mandible UK is stored. The sensors OS1 or US1, respectively, are entered and/or modeled in the 30 model. Once the positions relative to the transmitter coil 8 are known via the sensors, the 3D models of the maxilla OK or the mandible UK, respectively, can also be virtually arranged in the correct position in relation to one another. An overall model can thus be formed, in which the 3D models of the mandible UK and the maxilla OK are positioned in the correct location in relation to one another, and therefore the relative position in relation to one another is determined. A relative movement of the maxilla OK and the mandible UK can also be represented in the overall model. The overall model can then be output via an interface 7, in order to be able to be used further, for example in a virtual articulator and/or in a CAD system. In particular, the device enables a movement sequence to be output, wherein the movement sequence comprises multiple complex individual movement sequences such as opening, closing, chewing, etc., and to be represented, for example, like a film. In this manner, movement paths of the mandible relative to the maxilla can be determined.

The 3D models of the maxilla or the mandible, respectively, are provided, for example, via an intraoral scanner 9, which records the maxilla OK or the mandible UK, respectively, using the applied sensors. Alternatively thereto, an imprint of the maxilla OK or mandible UK, respectively, with an imprint of the sensors is digitized via a 3D scanner 10, in order to obtain the 3D models.

Figure 3:
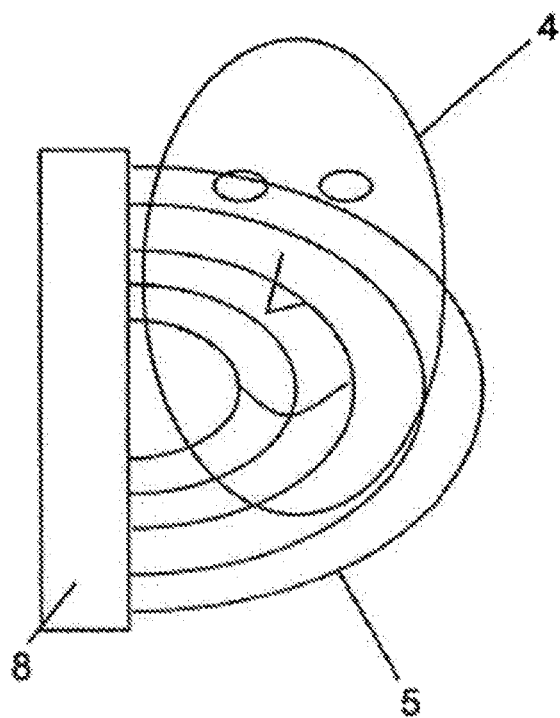
FIG. 3 shows a schematic illustration of a measurement configuration.
Figure 4:
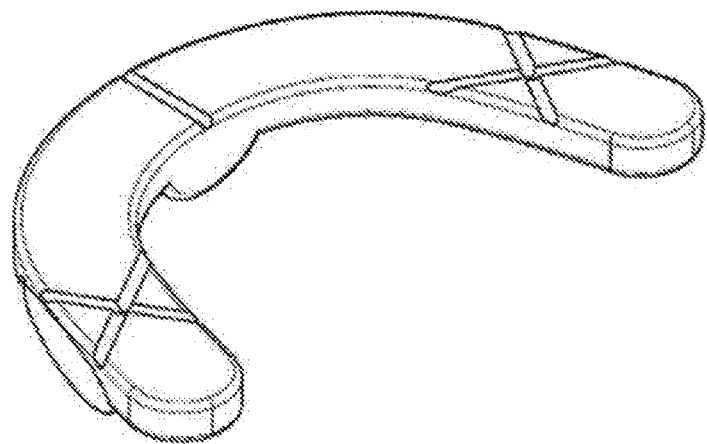
Figure 5:
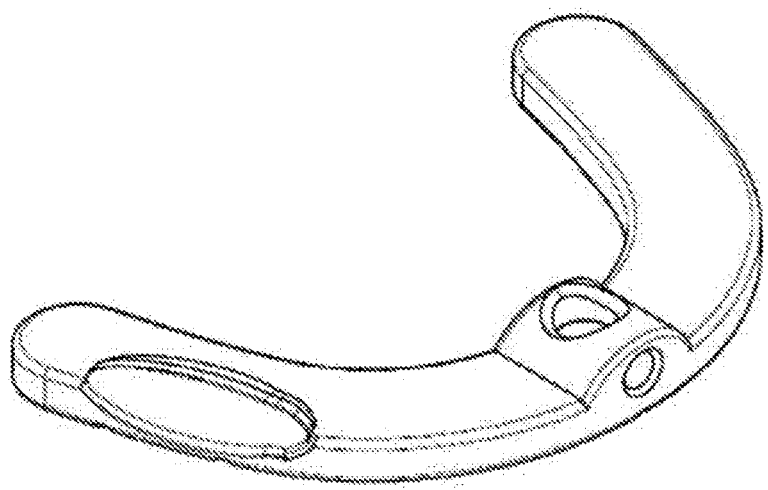
Figure 6:
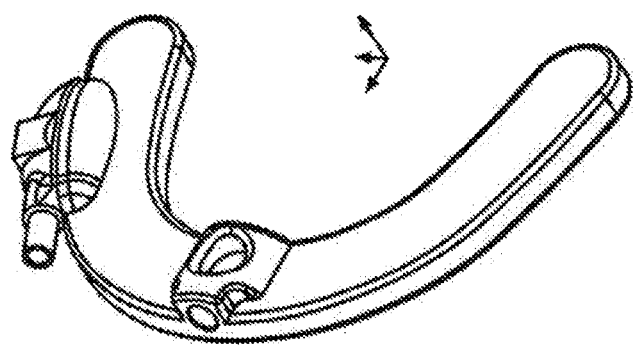
Figure 7:
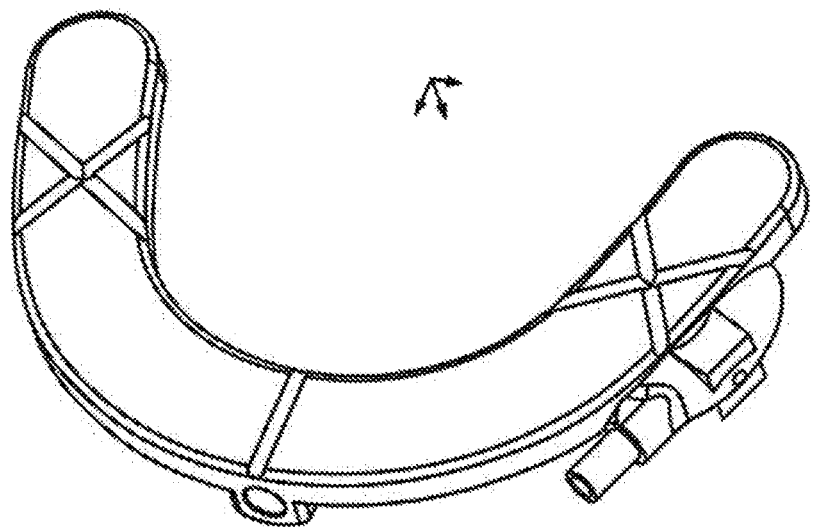

The measurement configuration is shown very schematically in FIG. 3, wherein it can be seen that the transmitter coil 8 is arranged outside the head 4 of the patient and specifically on one side, and therefore the measurement field 5 radiates through the head 4 from the side. The transmitter coil 8 is arranged in a stationary manner and/or independently from the patient. The measurement volume is 30 cm$^3$ to 50 cm$^3$.

Various diagonal views of a U-shaped bite plate 800 for a maxilla or mandible for toothless patients are shown in FIGS. 4-7. FIG. 8 additionally shows in detail a distancing unit having bite plates, wherein the bite plates are arranged between mandible and maxilla.

The distancing unit is used to establish the occlusal plane and for bite registration during the production of a total maxilla and/or mandible prosthesis.

The distancing unit comprises bite plates, wherein one bite plate is arranged on the mandible and one bite plate is arranged on the maxilla.

By way of setting the pin with ball in the vertical direction and inclination, the distancing unit can determine the correct location and inclination of the jaws in relation to one another and facilitates the measuring of the occlusal plane for the production of prostheses.

Alternatively, the distancing unit can have multiple pins, wherein the pins are arranged in the rear and/or lateral region of the bite plates and do not have a ball joint.

The bite plate particularly advantageously enables the patient to independently find an anatomically correct condyle position, even if it was previously lost.

Moreover, a UK recording can be produced on toothless patients using the unit for attaching the markers.

The respective bite plate has a centrally arranged pin 802 or multiple pins, wherein at least the pin has a ball 804 having a threaded borehole, in which the pin is arranged such that it is at least vertically adjustable, cf. FIG. 8. The bite plates consist of a metal foot, pin, and ball head and a plastic plate, which can be screwed onto the ball head using a hexagonal socket. The pin-ball base is fixed via the metal foot on the model in the tray material (plastic) respectively in the maxilla and mandible. The two bite plates are set in an average vertical height in the maxilla and mandible in this case and act freely in relation to one another in the mouth of the patient. Firstly the OK plate is aligned in the mouth of the patient (ala-tragus line, bipupillary line) and locked via a screw. Subsequently, the patient bites and the UK plate independently orients itself without action of the dentist. Subsequently, the dentist can encrypt the bite plates with one another.

FIGS. 9-11 show a schematic side view, top view, and diagonal view of a sensor shoe 900, which is fastenable on the respective teeth or a mandible accessory of the mandible (UK) or a maxilla accessory of the maxilla (OK). The sensor shoe is selected in terms of its shape with a slightly curved sole in such a manner that it can be easily adhesively bonded on the teeth and can be used even in constricted space conditions.

A position marking 902 is formed as an indentation or recess in the curved surface region 904 of the sensor shoe facing away from the respective tooth. In particular, the position marking is formed as a conical recess, and therefore its tip defines a zero point of the relationship of the sensor to the relative position and/or relative movement of the mandible (UK) relative to the maxilla (OK). The tip of the position marking is in a direct relationship to a planar surface region around the recess of the sensor shoe, wherein the sensor position is defined with respect to the relative position and/or relative movement of the mandible (UK) relative to the maxilla (OK).

A position marking is formed as an indentation or recess in the curved surface region of the sensor shoe facing away from the respective tooth. In particular, the position marking is formed as a conical recess, and therefore its tip defines a zero point of the relationship of the sensor to the relative position and/or relative movement of the mandible (UK) relative to the maxilla (OK). The tip of the position marking is in a direct relationship to a planar surface region around the recess of the sensor shoe, wherein the sensor position is defined with respect to the relative position and/or relative movement of the mandible (UK) relative to the maxilla (OK).

Figure 12:
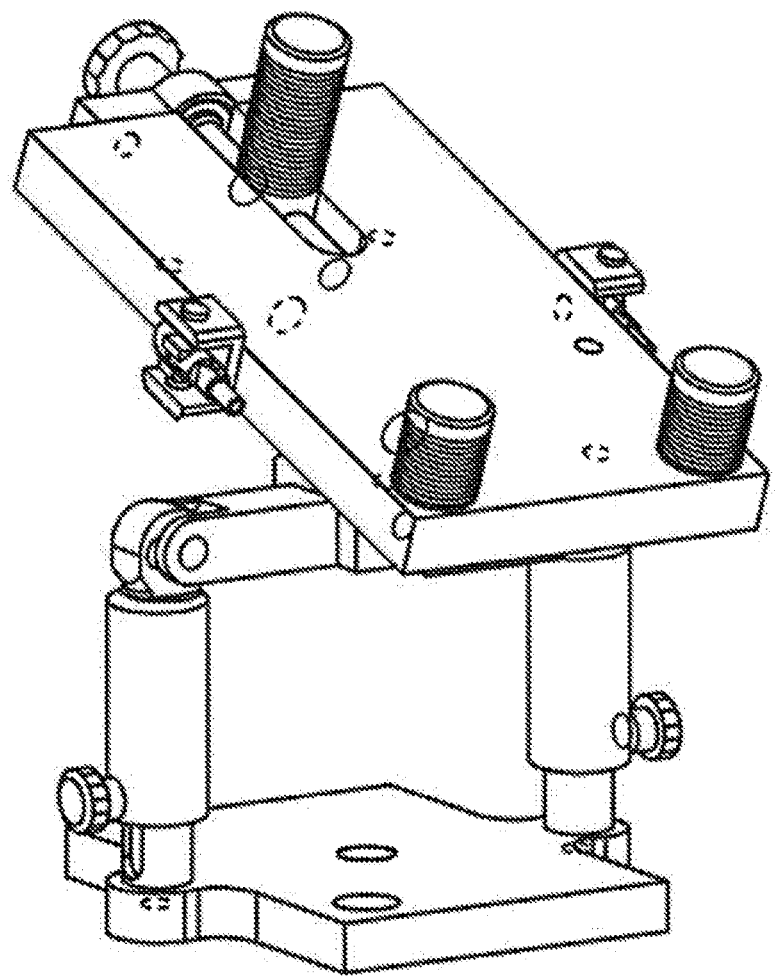
FIG. 12 shows an articulator.
Figure 13:
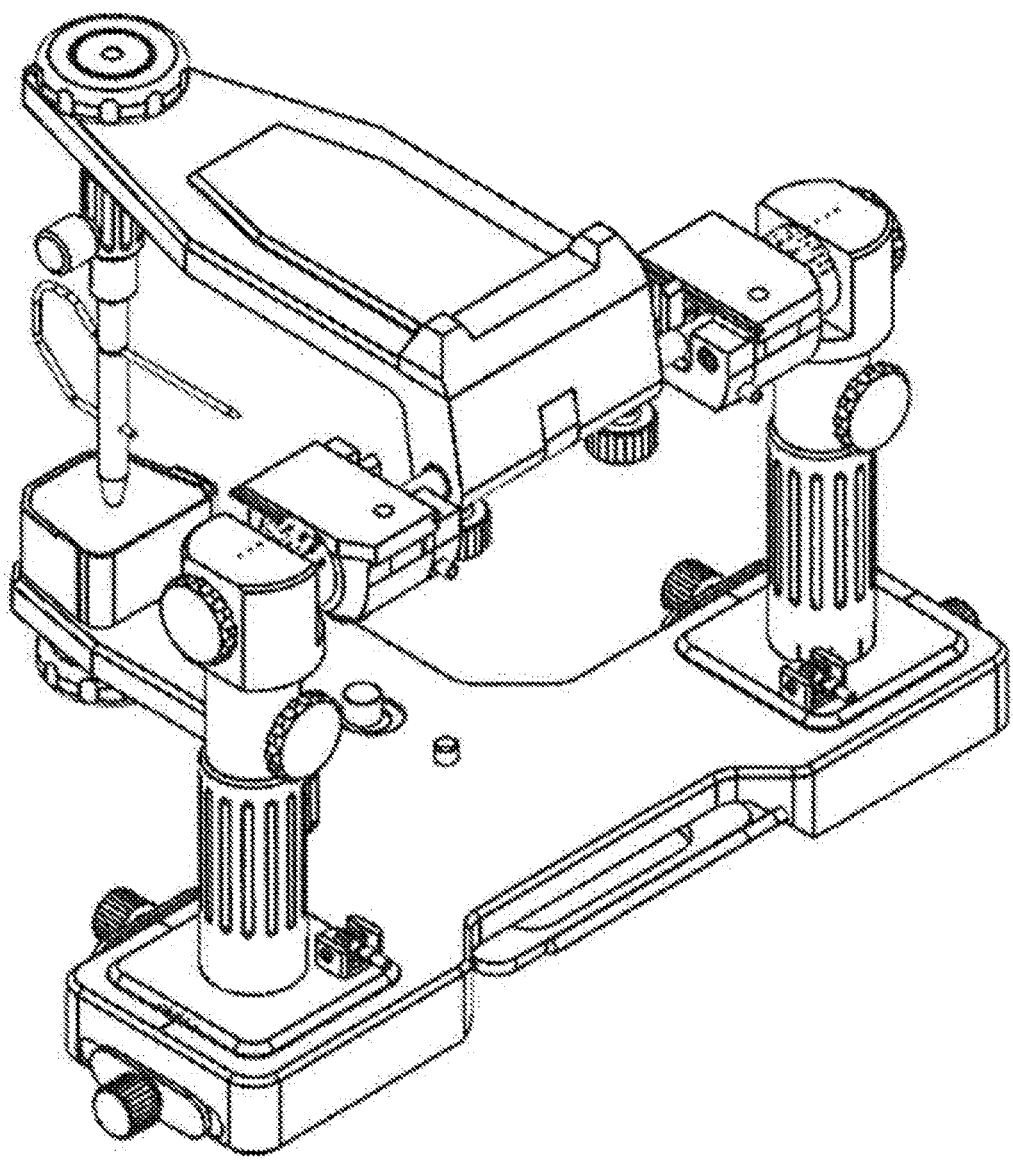
FIGS. 13 and 14 show a transfer table comprising movement simulator.
Figure 14:
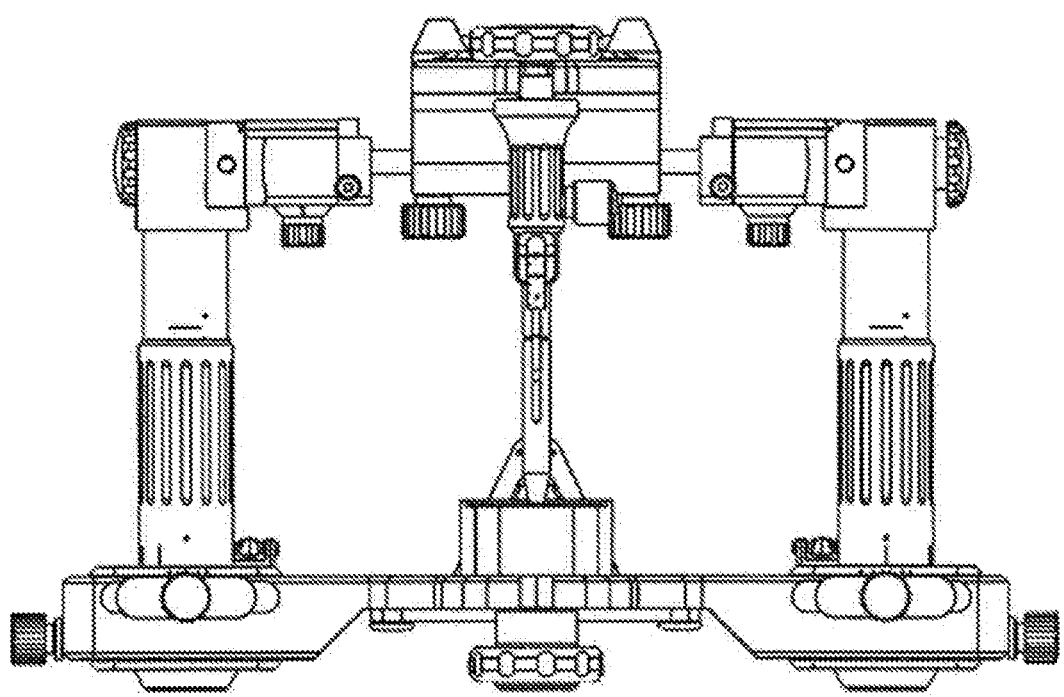

FIG. 12 shows a suitable transfer table and FIGS. 13 and 14 show an articulator as a movement simulator for the transfer and simulation and a previously measured relative movement of a mandible (UK) relative to a maxilla (OK) of a patient.

The magnetic field generator and the sensor shoes/markers are used for transferring the positions in the mouth by means of corresponding software to the transfer table, wherein the magnetic field generator is positioned at the worktable. The sensor/marker position at the transfer table is compared to the position in the mouth of the patient via the software. The correct positioning of the plaster model in the transfer table is indicated via the sensor shoes/markers fastened here via the software.

The articulator or movement simulator simulates the movements recorded in the mouth. To be able to set a therapeutic position in the case of patients or also total prosthesis wearers, markers can also be attached to the movement simulator, which are then in turn actuated via the software.

Via micrometer screws, x, y, and z axes can be adjusted and the therapeutic situation can thus be defined and established in the software, wherein the condyle boxes and condyle axes are also adjustable, since the condyles are located at different distances from one another in different people.

The movement sequence is completely created in the movement simulator, and therefore movement paths are compared to a UK movement acquisition created according to the dental prosthesis classification.

Irritation of the patient is completely avoided and free movements including chewing are possible during the UK movement recording for the first time.

LIST OF REFERENCE SIGNS

1 device
2 cable connection
3 analysis unit
4 head
5 electromagnetic measurement field
6 storage unit
7 interface
8 transmitter coil
9 intraoral scanner
10 3D scanner
D triangle
K coordinate system
O1-8 teeth
OD triangle
OE plane
OK maxilla
OS1 maxilla sensor
U1-8 teeth
UK mandible
US1 mandible sensor

The invention claimed is:

1. A device for measuring a relative position and/or relative movement of a mandible relative to a maxilla of a patient, the device comprising:
a transmitter coil for emitting a magnetic measurement field, wherein the transmitter coil is arrangeable extraorally laterally to or above the maxilla,
a mandible accessory designed as a first bite plate for setting a vertical position of the mandible,
a maxilla accessory designed as a second bite plate for setting a vertical position of the maxilla,
a plurality of holding units, each of the plurality of holding units designed as a sensor shoe, which can be adhesively bonded on teeth of the mandible or the maxilla of the patient, the maxilla accessory, or the mandible accessory, wherein the sensor shoe has at least one curved surface region oriented facing toward a tooth in use with at least one position marking defined in a second curved surface region facing away from the tooth,
a mandible sensor arrangeable intraorally, the mandible sensor accommodated in a first holding unit of the plurality of holding units, the first holding unit fastenable on the teeth of the mandible or on the mandible accessory, the mandible sensor designed at least for determining a position in the measurement field and/or in relation to the transmitter coil,
a maxilla sensor arrangeable intraorally, the maxilla sensor accommodated in a second holding unit of the plurality of holding units, the second holding unit fastenable on the teeth of the maxilla or on the maxilla accessory, the maxilla sensor designed at least for determining a position in the measurement field and/or in relation to the transmitter coil, and
an analysis unit for determining the relative position and/or relative movement of the mandible relative to the maxilla on the basis of the positions determined by the mandible sensor, the maxilla sensor, or both.

2. The device as claimed in claim 1, characterized in that the first bite plate is U-shaped.

3. The device as claimed in claim 1, characterized in that the first bite plate has a centrally arranged pin.

4. The device as claimed in claim 3, characterized in that the centrally arranged pin has a ball having a threaded borehole, in which the centrally arranged pin is arranged such that it is at least vertically adjustable.

5. The device as claimed in claim 1, characterized in that the mandible sensor, the maxilla sensor, or both each determine at least two rotational degrees of freedom, three rotational degrees of freedom, or six degrees of freedom in the measurement field and/or relative to the transmitter coil.

6. The device as claimed in claim 1, characterized in that the maxilla sensor is either one of two maxilla sensors, each of the two maxilla sensors having five degrees of freedom or one maxilla sensor having six degrees of freedom arranged on the maxilla, and the mandible sensor is either one of two mandible sensors, each of the two mandible sensors having five degrees of freedom, or one mandible sensor with six degrees of freedom arranged on the mandible.

7. The device as claimed in claim 1, characterized in that in use a distance between the mandible sensor and the tooth to which the mandible sensor is configured to be fastened to is less than 0.5 cm.

8. The device as claimed in claim 1, characterized by a digitizing unit for creating a digital, three-dimensional model of the maxilla and/or the mandible, wherein the digitizing unit is configured to model the holding units and/or sensors in the model.

9. The device as claimed in claim 8, characterized in that the digitizing unit is designed as an intraoral scanner or as an intraoral camera.

10. A method for determining a relative position and/or relative movement of a mandible relative to a maxilla of a patient using a device of claim 1, comprising the following steps:

arranging the mandible sensor of the device of claim 1 on the mandible, wherein the first holding unit accommodates the mandible sensor and is fastened on the mandible and/or adhesively bonded on the teeth;

recording sensor signals of the mandible sensor;

determining a relative position and/or relative movement between the maxilla and the mandible on the basis of the mandible sensor signals.

11. The method as claimed in claim 10, comprising the following step:

creating a digital, three-dimensional model of the maxilla and/or the mandible, wherein the plurality of holding units, the mandible sensor, and the maxilla sensor are modeled in the model, and fusing the three-dimensional model with the determined relative position and/or relative movement to generate an image of a movement sequence.

12. The method as claimed in claim 11, characterized in that fusing the three-dimensional model with the determined relative position and/or relative movement includes fusing the three-dimensional model with the determined relative movement and the movement sequence comprises multiple complex individual movement sequences.

13. The device as claimed in claim 1, characterized in that the position marking is formed as a conical recess, and/or characterized in that the position marking is arranged centrally on the sensor shoe.

14. The device as claimed in claim 13, characterized in that a tip of the position marking is located on a planar surface region of the recess of the conical sensor shoe.

15. A holding unit for at least one maxilla sensor or at least one mandible sensor for use in a device for measuring a relative position and/or relative movement of a mandible relative to a maxilla of a patient, wherein the holding unit is fastenable on the maxilla or on the mandible, wherein the holding unit is designed as a sensor shoe, which can be adhesively bonded on respective teeth or a mandible accessory of the mandible or a maxilla accessory of the maxilla and the sensor shoe has a first curved surface region oriented facing toward a tooth in use with at least one position marking defined in a second curved surface region facing away from the tooth in use, the position marking is formed as a conical recess, a tip of which defines a zero point of the relationship of the at least one maxilla sensor or the at least one mandible sensor disposed in the holding unit to the relative position and/or relative movement of the mandible relative to the maxilla.

16. The holding unit as claimed in claim 15, characterized in that the tip of the position marking is located on a planar surface region of the conical recess of the sensor shoe.

17. The holding unit as claimed in claim 15, characterized in that the position marking is arranged centrally on the sensor shoe.

18. The holding unit as claimed in claim 15, characterized in that the sensor shoe is designed for interlocking accommodation of a first maxilla sensor and a first mandible sensor of the at least one maxilla sensor and/or at least one mandible sensor.

\* \* \* \* \*

UNITED STATES PATENT AND TRADEMARK OFFICE
CERTIFICATE OF CORRECTION

PATENT NO. : 11,452,585 B2
APPLICATION NO. : 16/081779
DATED : September 27, 2022
INVENTOR(S) : Petra Clauss It is certified that error appears in the above-identified patent and that said Letters Patent is hereby corrected as shown below:

In the Claims

Column 12, Line 11, Claim 14, delete "recess of the conical" and insert -- conical recess of the --

Signed and Sealed this
Twenty-ninth Day of November, 2022

Katherine Kelly Vidal
*Director of the United States Patent and Trademark Office*